United States Patent
Owens et al.

(10) Patent No.: US 7,587,234 B2
(45) Date of Patent: Sep. 8, 2009

(54) METHOD AND APPARATUS FOR COMPUTER MODIFIED MAGNETIC RESONANCE IMAGING

(75) Inventors: Timothy R. Owens, Dublin, CA (US); James M. Cannon, Jr., Santa Clara, CA (US); Gregory Matthew Hyde, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 758 days.

(21) Appl. No.: 10/008,456

(22) Filed: Nov. 2, 2001

(65) Prior Publication Data

US 2003/0088178 A1   May 8, 2003

(51) Int. Cl.
*A61B 5/05* (2006.01)
(52) U.S. Cl. .................. 600/420; 600/423; 600/424; 600/426; 600/427; 600/429
(58) Field of Classification Search .............. 600/411, 600/417, 423, 424, 427, 429, 433, 420, 410, 600/414, 407, 439, 408, 425, 426, 428
See application file for complete search history.

(56) References Cited

U.S. PATENT DOCUMENTS

| 4,989,608 | A |   | 2/1991  | Ratner |
|---|---|---|---|---|
| 5,154,179 | A | * | 10/1992 | Ratner ........................ 600/420 |
| 5,728,079 | A |   | 3/1998  | Weber et al. |
| 5,744,958 | A |   | 4/1998  | Werne |
| 5,817,017 | A | * | 10/1998 | Young et al. ................. 600/433 |
| 5,868,674 | A |   | 2/1999  | Glowinski et al. |
| 5,873,822 | A | * | 2/1999  | Ferre et al. ................... 600/407 |
| 5,873,823 | A | * | 2/1999  | Eidelberg et al. ........... 600/407 |
| 5,908,410 | A |   | 6/1999  | Weber et al. |
| 6,007,544 | A |   | 12/1999 | Kim |
| 6,015,429 | A |   | 1/2000  | Lau et al. |
| 6,152,933 | A | * | 11/2000 | Werp et al. ................... 606/130 |
| 6,167,292 | A | * | 12/2000 | Badano et al. .............. 600/407 |
| 6,226,543 | B1 |  | 5/2001  | Gilboa et al. |
| 6,272,370 | B1 | * | 8/2001  | Gillies et al. ................ 600/411 |
| 6,490,473 | B1 | * | 12/2002 | Katznelson et al. ......... 600/410 |

\* cited by examiner

*Primary Examiner*—Brian Casler
*Assistant Examiner*—Baisakhi Roy
(74) *Attorney, Agent, or Firm*—Blakely Sokoloff Taylor & Zafman LLP

(57) ABSTRACT

A device is presented including a medical device adapted to be inserted in an anatomy. The medical device has many target markers. A magnetic resonance imaging (MRI) system will not detect or will disregard the medical device as noise without information obtained on the plurality of target markers prior to insertion of the medical device into the anatomy. Also presented a method including inserting a medical device into an anatomy. The medical device has many target markers. Scanning a magnetic resonance image (MRI) of the anatomy. Processing the scanned image by a MRI processor connected to a memory. Determining a location and orientation of the medical device in relation to the anatomy based on the target markers. And displaying a precise image of the medical device within the anatomy. The medical device is not detectable or disregardable as noise for MRI systems.

42 Claims, 10 Drawing Sheets

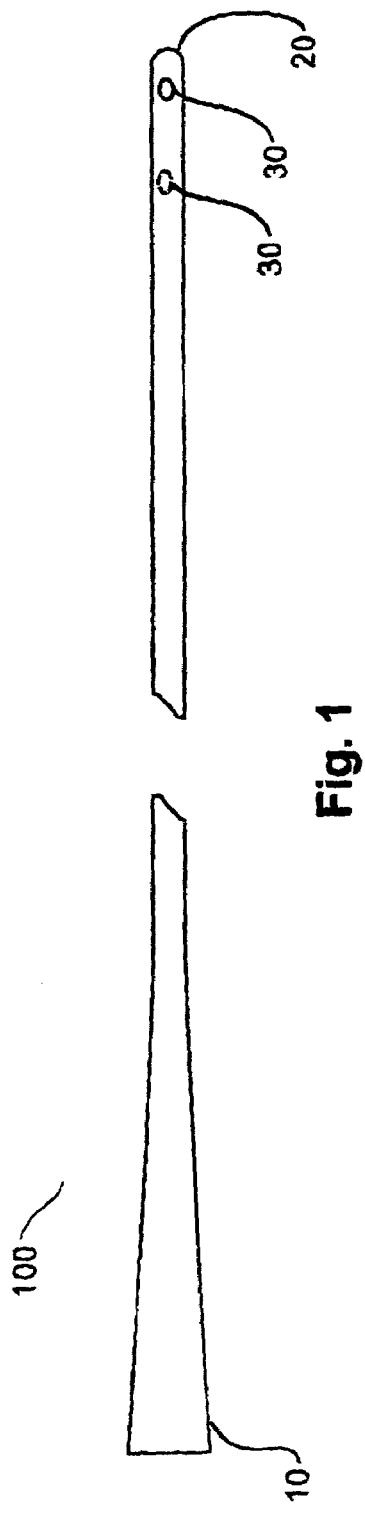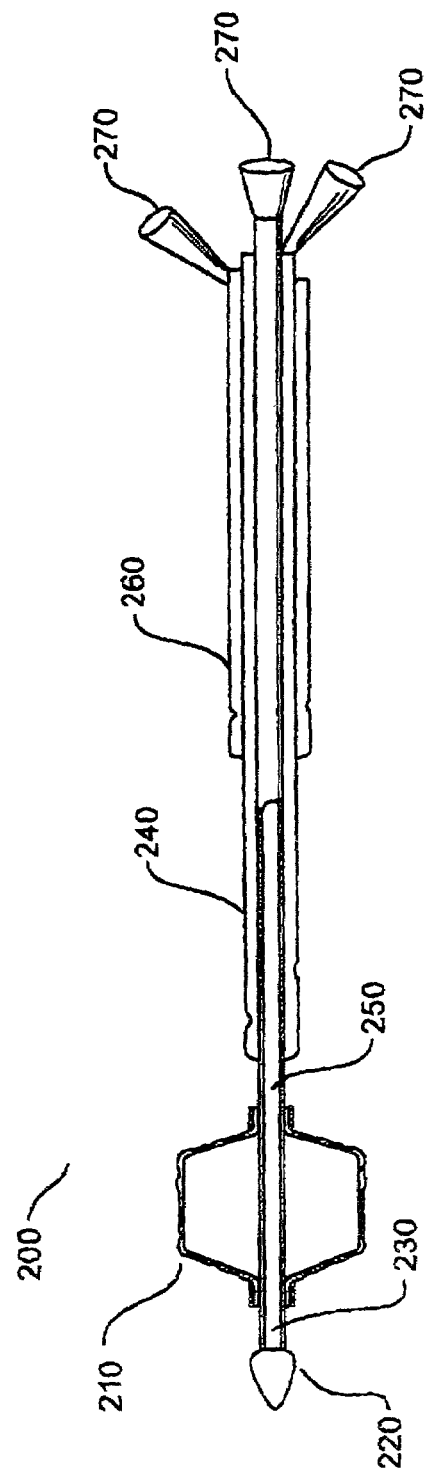

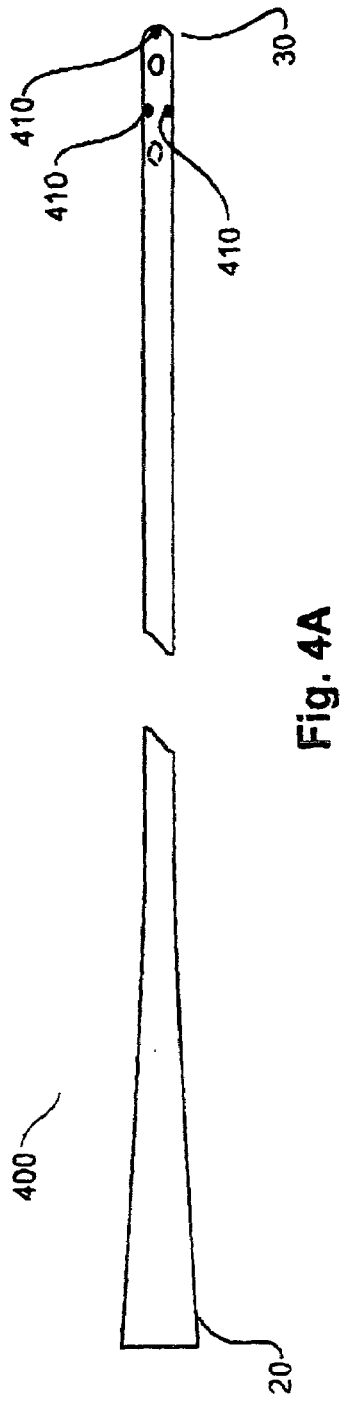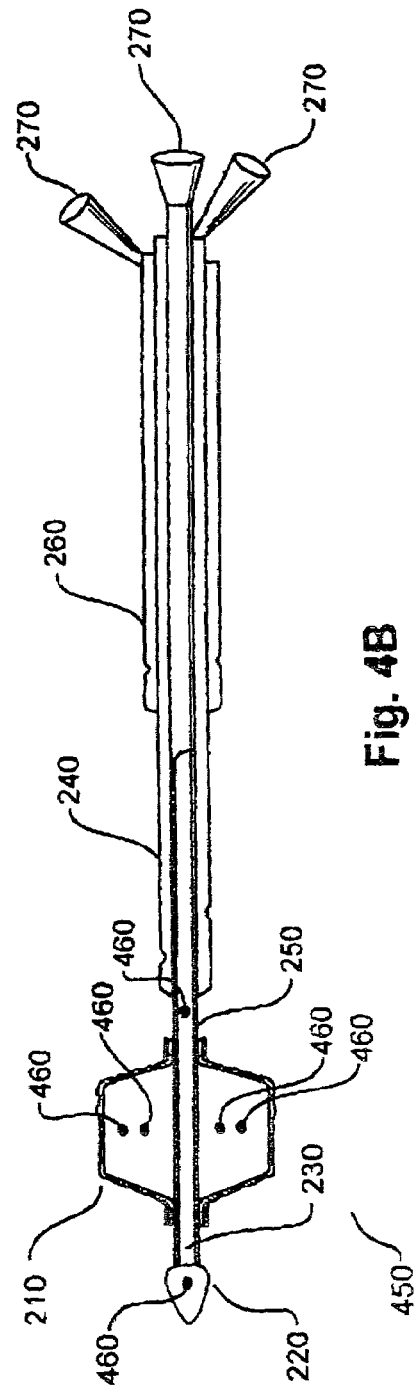

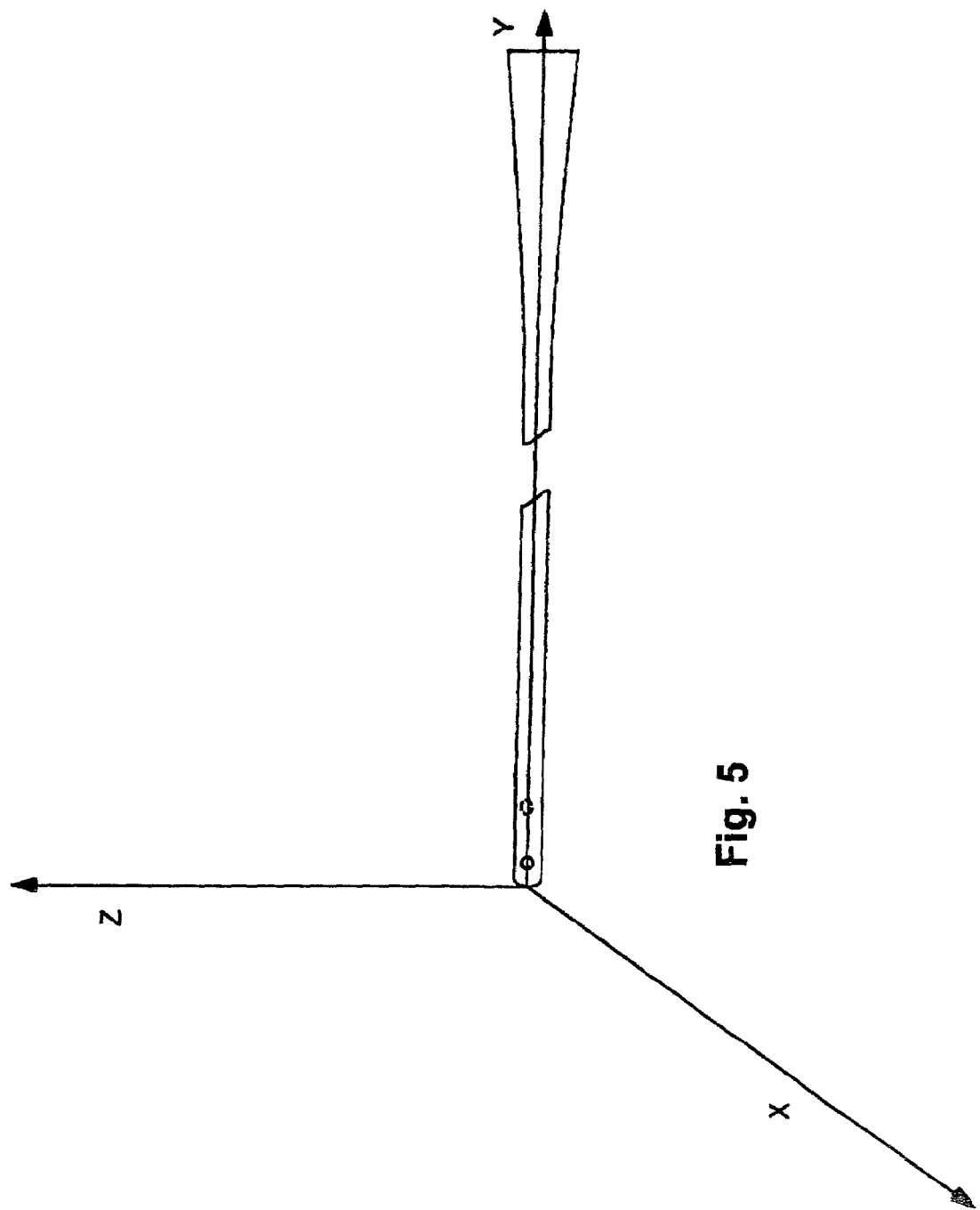

ME THOD AND APPARATUS FOR COMPUTER MODIFIED MAGNETIC RESONANCE IMAGING

BACKGROUND

1. Field of the Invention

This invention relates to magnetic resonance imaging (MRI), and more particularly to a method and apparatus to modify MRI processors to detect low-level signals not ordinarily detected and to enhance visualization of surgical devices in an anatomy.

2. Description of the Related Art

Magnetic Resonance Imaging (MRI) is an imaging technique primarily used in medical settings to produce high-quality images of the internal human body. MRI is based on principles of Nuclear Magnetic Resonance (NMR), a spectroscopic technique used by scientists to obtain microscopic chemical and physical information about molecules.

The human body consists primarily of fat and water. Fat and water have many hydrogen atoms that make the human body approximately 63 percent hydrogen atoms. The nucleus of a hydrogen atom is comprised of a single proton. A property called "spin" is possessed by a single proton in a hydrogen atom. Spin can be thought of as a small magnetic field that causes the nucleus to produce an NMR signal.

During magnetic resonance imaging, an MRI system generates a strong magnetic field. When a target object (containing water molecules or other hydrogenous compounds) is positioned in the field, the field aligns magnetic dipoles of the hydrogen nuclei within the water molecules (and other hydrogen atoms). The magnetic field strength required to so align the magnetic dipoles is typically on the order of one Tesla, but field strengths significantly higher and lower than one Tesla are also used in various applications of MRI. The magnetic field imparts a resonant frequency to the nuclei that is proportional to the field strength. Once aligned by the magnetic field, the magnetic dipoles can be rotated out of alignment by application of radio frequency (RF) energy at the resonant frequency of the system. Electromagnetic radiation is subsequently emitted by the resonating magnetic dipoles (i.e., the protons spinning at their resonance frequency), as they return to alignment with the field. Imaging occurs as a result of detecting such radiation emitted from each of many different regions within the target.

Physicians use catheters and other medical devices (e.g., scalpels, forceps, retractors, biopsy needles, etc.; and implanted devices used for therapy such as sutures, pacemakers, stents, shunts, orthopaedic devices, dental devices, etc.) to treat patients. Various techniques can be used to monitor these devices while internal to the patient to insure proper administration of a medical technique or post treatment for implanted devices.

Devices, such as X-ray machines, are used to monitor the medical device while internal to a patient. MRI systems can also aid doctors in visualizing medical devices while internal to a patient. It is typically desired that the MRI system portray one or more of the instruments while also imaging a selected portion of the patient. For example, it may be desirable to visualize a biopsy needle or catheter inserted in the tissue of the patient. In addition, it is also desirable to have permanently implanted medical devices such as blood filters, stents, or other such implants visualized in the MR image without affecting the image quality of the surrounding tissue structures.

In magnetic resonance therapy (MRT), the presence of both the magnetic and RF fields used in the imaging process place several constraints on each device to be positioned or manipulated near or in the imaging region of an MRI system. One constraint is that the device must be essentially non-ferromagnetic, so that it is not attracted by a magnetic field. This consideration applies to any object that is implanted within a patient being imaged. This is because the magnetic field would subject such an object to undesirable forces and torque's if it were made entirely of ferromagnetic material. Another constraint is that an electrical instrument must be tolerant of the static and pulsed magnetic and RF fields, in the sense that it can function in the presence of these fields. A further constraint is that a metallic implant or other metallic instrument should not be subject to significant induction heating due to the applied RF field. And, the device should not create imaging artifacts that obscure or distort the image of the target.

Because of these typical constraints, devices used in MRT operations have conventionally been made of non-ferromagnetic metal such as titanium, nitinol, some types of stainless steel, aluminum, copper, or brass. Such non-ferromagnetic metal devices, however, have the following undesirable imaging property when imaged together with a patient in an MRI system. The non-ferromagnetic metal devices, just as most non-hydrogenous materials, will be "negatively" imaged by the MRI system as a black void. That is, the device displaces tissue that normally would be imaged. In areas where the patient's tissue structure has a dark gray or black appearance (due to a weak or absent radiation signal from the magnetic dipoles of its water molecules), the negative image (void) created by the device worsens visualization.

Also, metallic, non-ferromagnetic materials (unless they are ultra-thin) may cause unacceptable imaging artifacts when imaged by an MRI system. Such artifacts (which can have the appearance of a halo or glow around the material which would obscure or distort the image of any target material) occur because the presence of the RF field sets up eddy currents in the non-ferromagnetic material, which in turn create inhomogeneities in the magnetic field of the MRI system. In addition, imaging artifacts are caused by incompatibilities in the magnetic susceptibilities of materials that are in the imaging field.

Other devices are made of polymer materials (such as catheters). These devices are hydrogenous and can obscure imaging of a target since the device may be more hydrogenous than the target. Or, the tissue may be more hydrogenous than the device, thus, obscuring the device. Therefore, MRI systems are not capable of detecting all medical devices while internal to a patient, unless these devices have been modified with suitable material for the MRI system to detect the device. By modifying medical devices to contain a means for a typical MRI system to detect the device, the device's structure is modified.

In the case of medical devices, such as catheters (e.g., catheter body balloon, etc.), an MRI system cannot usably detect the device because the device may cause "noise" that distorts the desired image. The device can cause negative imaging (black spots or image faults). Also, some catheter device components have no impact on a desired MRI image. In other words, the device's components do not appear in the image. Therefore, the MRI image will visualize the same with or without the catheter device in place internal to a patient.

Black spots may appear in an MRI image when the central-processor of the MRI system does not recognize the signal from the medical device as valid data. This is due to the central-processor for the MRI system not having sufficient logic to resolve the signal from the medical device. Therefore, the reported image is not precise, and the device appears as black spots in the MRI image, hence the MRI system discards the imprecise data.

In other instances, a medical device does not show up at all in an MRI image. Typically, the central-processor for the MRI system does not recognize the signal from the medical device, so the central-processor sorts the signal as invaluable outlier data, or noise. Thus, the central-processor filters the signal out, to produce a precise anatomic image without the medical device present in the MRI image.

What is needed is a technique and system to accurately display/identify a medical device in an MRI image while that device is internal to a patient. A medical device capable of being accurately displayed/identified in an MRI image while internal to a patient is also needed.

SUMMARY

A medical device adapted to be inserted in an anatomy is presented. The medical device includes a plurality of target markers. A magnetic resonance imaging (MRI) system will not detect or will disregard the medical device as noise. In some embodiments, the target markers may be either ferromagnetic or paramagnetic material.

Also provided is a system including a MRI processor. The processor includes a low-level signal detection process stored in a memory. A MRI scanner connected to the processor is also included. In addition, the system includes a control unit and a display connected to the processor. Further included is a medical device adapted to be inserted in an anatomy. The medical device includes many target markers. The medical device is either not detectable or disregardable for MRI systems not having a low-level signal detection process.

In one embodiment, the system includes a pre-scanning device connected to the processor. In one embodiment the pre-scanner transmits either geometric data, image data, or geometric data and image data of a medical device to the processor.

In one embodiment an image of the medical device is superimposed over its precise location within the anatomy. Also, the superimposed image has the precise orientation that the medical device has within the anatomy.

In one embodiment, pixels of the medical device replace a plurality of pixels of an anatomy at the precise location that the medical device is located at within the anatomy. The pixels of the medical device have the precise orientation that the medical device has within the anatomy.

A method is provided where a medical device having target markers is inserted into an anatomy. The method includes scanning a MRI of the anatomy, processing the scanned image by a MRI processor connected to a memory, determining a location and orientation of the medical device in relation to the anatomy based on the target markers, and displaying a precise image of the medical device within the anatomy. The medical device is either not detectable or disregardable for MRI systems that do not include a low-level signal detection process.

In one embodiment, the method includes pre-scanning the medical device before inserting the medical device in an anatomy, and transmitting either geometric data, image data, or geometric data and image data of the medical device and the plurality of target markers to the MRI processor.

In one embodiment the target markers include either ferromagnetic or paramagnetic material. In one embodiment, the method includes superimposing an image of the medical device over the anatomy. The superimposed image of the medical device is located at its precise location within the anatomy. The superimposed image also has the precise orientation that the medical device has within the anatomy.

In one embodiment, the method includes replacing many pixels of an anatomy with many pixels of the medical device at the precise location that the medical device is located at within the anatomy. The pixels of the medical device have the precise orientation that the medical device has within the anatomy.

Also presented is a device including a machine-readable medium containing instructions which, when executed by a machine, cause the machine to perform operations including instructions that cause the machine to scan a MRI of the anatomy, process the scanned image by a MRI processor connected to a memory. The MRI processor has a low-level signal detection process. Further included are instructions that cause the machine to determine a location and orientation of a medical device in relation to the anatomy based on target markers, and to display a precise image of the medical device within the anatomy. The medical device is either not detectable or disregardable for MRI systems without the low-level signal detection process.

In one embodiment, the device includes instructions which, when executed by the machine, cause the machine to perform operations to pre-scan the medical device before inserting the medical device in an anatomy, and to transmit either geometric data, image data, or geometric data and image data of the medical device and the plurality of target markers to the MRI processor.

In one embodiment the device includes instructions which, when executed by the machine, cause the machine to perform operations to superimpose an image of the medical device over the anatomy. The superimposed image of the medical device is located at its precise location within the anatomy. The superimposed image has the precise orientation that the medical device has within the anatomy.

In one embodiment the device includes instructions which, when executed by the machine, cause the machine to perform operations to replace pixels of an anatomy with pixels of the medical device at the precise location that the medical device is located at within the anatomy. The pixels of the medical device have the precise orientation that the medical device has within the anatomy.

In one embodiment the device includes instructions which, when executed by a machine, cause the machine to perform operations of scanning a magnetic resonance image (MRI) of an anatomy. The scanned image is processed by a MRI processor connected to a memory. The MRI processor has a low-level signal detection process. A location and orientation of the medical device in relation to the anatomy is determined based on detection of many target markers in relation to the medical device and each of the many target markers. The many target markers and geometric data of the medical device is determined before the medical device is inserted into the anatomy. A precise image of the medical device within the anatomy is displayed. The medical device is either not detectable or disregardable as noise for MRI systems without the low-level signal detection process.

In one embodiment a system includes a magnetic resonance imaging (MRI) processor. The processor includes a low-level signal detection process stored in a memory. A MRI scanner is connected to the processor. A control unit is connected to the processor. A display is connected to the processor. A medical device to be inserted in an anatomy is included. The medical device has many target markers. The medical device is either not detectable or disregardable as noise for MRI systems without the low-level signal detection process. Prior to insertion of the medical device into the anatomy, location and orientation of the medical device in relation to the anatomy is determined by the processor based on detection of the many target markers in relation to the geometric information of the medical device and each of the many target markers. Geometric information of the medical device and the many target markers is obtained before the medical device is inserted into the anatomy.

BRIEF DESCRIPTION OF THE DRAWINGS

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

FIG. 1 illustrates a typical catheter that is adapted to be inserted into an anatomy.

FIG. 2 illustrates a balloon type catheter.

FIG. 4A illustrates an embodiment of a catheter having target markers embedded or attached to a catheter device.

FIG. 4B illustrates an embodiment of a balloon catheter having target markers embedded or attached thereto.

FIG. 5 illustrates an embodiment of a distal end of a catheter having coordinates set to X=0, Y=0, Z=0.

DETAILED DESCRIPTION

Figure 3:
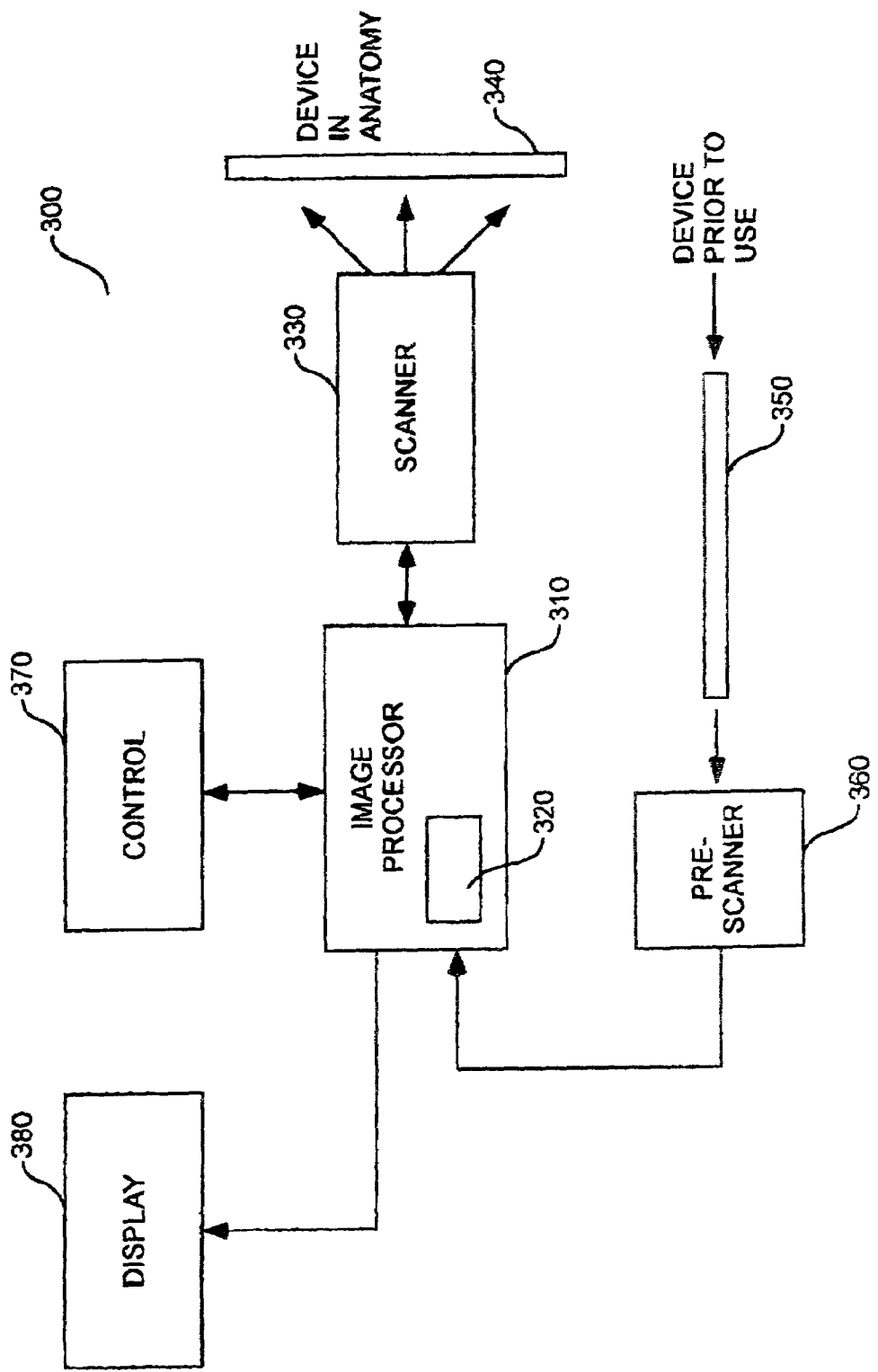
FIG. 3 illustrates an embodiment of a modified magnetic resonance imaging (MRI) system.

A method and apparatus for magnetic resonance imaging (MRI) processing to enhance visualization of surgical devices not ordinarily detectable by MRI systems is described. Referring to the figures, exemplary embodiments of the method and apparatus will now be described. The exemplary embodiments are provided to illustrate the invention and should not be construed as limiting the scope of the invention.

FIG. 1 illustrates a catheter body that is suitable for insertion into an anatomy, such as the vascular of a human or animal. The catheter illustrated in FIG. 1 can be used for delivering fluids into an anatomy. Catheter 1 includes a flexible tubular member formed of a flexible material, such as a polymer material (e.g., a polyethylene material). Catheter 1 includes funnel-shaped portion 10 at its proximal extremity, rounded-tip portion 20 at its distal extremity, and fluid delivering openings 30.

FIG. 2 illustrates balloon type catheter body 200 having inflatable balloon portion 210, tip 220, guide lumen 230, first-catheter jacket 240, first lumen 250, a second catheter jacket 260, and connecting members 270 facing away from an anatomy. Catheter 200 typically includes a flexible tubular member formed of a flexible material, such as a polymer material (e.g., polyethylene, etc.). Inflatable balloon portion 210 is made of an expandable material, such as latex, so that inflatable balloon portion 210 can be deployed within an anatomy at strategic locations.

The catheter bodies constructed solely of a polymer material illustrated in FIGS. 1 and 2 bodies constructed of a polymer material or having a metallic support mandrel may not show up on a MRI scanned image or may block out anatomy in a scanned image. To make the catheter bodies illustrated in FIG. 1 or 2 visible during MRI, the catheter bodies may be coated or impregnated with ferromagnetic or paramagnetic material. Typically, manufacturing techniques, such as pultrusion, extrusion, etc. are necessary to impregnate or coat portions of catheters (or other medical devices used in anatomy) to allow viewing of the medical devices inserted for various medical techniques.

The material (e.g., polymer material) for a catheter body such as catheter body 100 (FIG. 1) or catheter body 200 (FIG. 2) must have properties selected to be flexible enough to be snaked through the vascular. Such snaking can be over a considerable distance. Peripherally inserted catheters, for example, may be snaked from locations in a human arm or groin to an artery adjacent the heart (e.g., left coronary artery or left circumflex artery).

For catheters to be viewed in a MRI image, the ferromagnetic or paramagnetic material must be distributed throughout much or all of the catheter device. By having ferromagnetic or paramagnetic material either mixed into polymer as it is extruded, or distributed substantially uniformly throughout the catheter body, the properties of the catheter body are modified substantially by the addition of the material.

One alternative to substantially modifying the structural property of a catheter body or other temporarily or permanently implantable medical device is to locate ferromagnetic or paramagnetic markers at strategic locations. Although a typical MRI system (0.2-5.0 Tesla) would interpret such markers as noise and disregard, a MRI system may then be configured to operate at a level such that the markers are detected.

FIG. 3 illustrates an embodiment comprising a modified MRI system 300. System 300 includes a central-image processor 310, low-level signal detection process 320, which allows image processor 310 to detect low level signals of ferromagnetic or paramagnetic material on an inserted medical device in an anatomy, scanner 330, control unit 370, and display 380. Low-level signal detection process 320 is such that it can be loaded by conventional means, such as a computer floppy disk, a CD-ROM, via a network transfer onto system 300, etc. Therefore, low-level detection process 320 re-programs a typical MRI system to detect signals not detectable without low-level detection process 320 or modifies a typical MRI system by allowing the MRI system to use low-level signals that are typically ignored as noise. Typical MRI systems are programmed to discard signals at a threshold sensitivity level. Most threshold sensitivity levels are too high to detect a signal generated from a small amount of ferromagnetic or paramagnetic material on a medical device inserted into an anatomy. In some systems, the background signals are at such a level as to render the embodiments low level ferromagnetic or paramagnetic material on a medical instrument inserted in an anatomy undetectable. Therefore, with a background signal having a higher signal-to-noise ratio (SNR), the low-level signal produced from the low level ferromagnetic or paramagnetic material on a medical instrument inserted in an anatomy is discarded as noise in typical MRI systems without low-level signal detection process 320. Therefore, depending on the small amount of low level ferromagnetic or paramagnetic material to be coupled with a medical instrument, the MRI system threshold needs to be adjusted so as to not discard signals from the medical device as noise. One should note that the amount of low-level material coupled with a medical device should be such that the structure of the medical device is not modified in order to have the low-level material coupled with the medical device. Therefore, depending on the amount of material that can be coupled with the medical device so that the structure is not modified (and the amount is not dangerous to an anatomy), the MRI systems threshold for signal detection may need to vary per device. In one embodiment, the low-level detection process allows for a client of MRI system 300 to select a varying threshold of signal detection based on the type of medical device or the amount of known low-level material. In the case where pre-scanner 360 (discussed below) may be coupled to MRI system 300, once pre-scanner 360 scan a medical device outside an anatomy, low-level detection process 320 automatically adjusts the signal threshold based on the determined size or type of medical device.

In one embodiment, low-level detection process 320 preloads information regarding placement of the low-level ferromagnetic or paramagnetic material coupled with a medical instrument into a memory. In order to not discard the signal returned from the low-level material, low-level detection process compares the detected signal, after the detected signal is processed, with the known placement of the low-level material. Upon a match, the signals/data from the low-level material is not discarded.

MRI system 300 is used in conjunction with one embodiment having a medical device, such as a catheter, a balloon catheter, stent delivering devices, photographic medical devices, etc. that is used in medical techniques in an anatomy that are slightly modified with low-level ferromagnetic or paramagnetic material. The low-level ferromagnetic or paramagnetic material applied or inserted onto the medical device does not substantially modify the medical device's structure. One way the structural properties of a medical device are not substantially modified is by placing a ferromagnetic or paramagnetic material only at strategic locations to act as target markers.

FIG. 4A illustrates an embodiment of a catheter body 400 having target markers 410 embedded or attached thereon. Catheter body 400 is contains a polymer. "Polymer," "poly," and "polymeric" are defined as compounds that are the product of a polymerization reaction and are inclusive of homopolymers, copolymers, terpolymers etc., including random, alternating, block, and graft variations thereof. Representative examples of polymers that can be used with the embodiments of the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-cotrimethylene carbonate); polyphosphoester; polyphosphoester urethane; poly(amino acids); cyanoacrylates; poly(trimethylene carbonate); poly(iminocarbonate); copoly (etheresters) (e.g. PEO/PLA); polyalkylene oxalates; polyphosphazenes and biomolecules such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters; such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides; such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

FIG. 4B illustrates an embodiment having target markers 460 embedded or attached to balloon catheter device 450. Balloon catheter device 450 includes a body containing a polymer. It should be noted that fluid delivering and balloon catheters are used for illustration purposes and that other medical devices can be used besides these. Other devices include, but are not limited to, stent devices, photographic devices, etc.

Reference to FIG. 4A and FIG. 4B, in one embodiment, target markers 410 and 460 are include a material detectable by an MRI system. Examples of suitable material for target markers 410 and 460 include ferromagnetic or paramagnetic material. Target markers 410 are of such a low level of paramagnetic or ferromagnetic material that a typical MRI system cannot detect or will ignore as noise their presence on a medical device, such as a catheter. If a MRI system cannot detect or the system ignores the low-level paramagnetic or ferromagnetic material on a medical device (as noise), such as a catheter, the device will not be capable of being visualized as the anatomy is scanned during a typical MR imaging procedure.

Figure 4C:
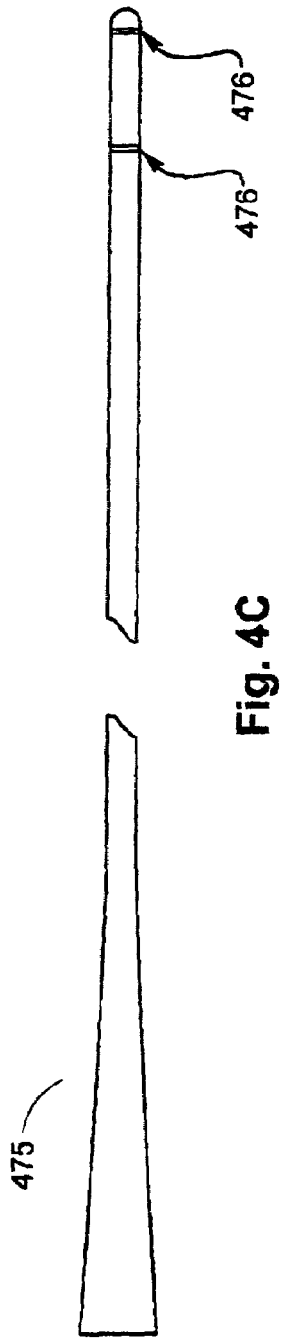
FIG. 4C illustrates an embodiment of a catheter having a band of target markers embedded or attached thereto.

FIG. 4C illustrates another embodiment of a catheter body having target markers embedded or attached thereto. In this embodiment, catheter body 475 includes target markers 476 containing thin (e.g., on the order of 0.0005-0.005 inches) bands of paramagnetic or ferromagnetic material that are embedded or attached to the perimeter of catheter 475 in a plurality of strategic locations, for example two. In this example, the two strategic locations may vary where the orientation of catheter 475 can be determined based on the location of target markers 476. Target markers 476 are of such a low level of paramagnetic or ferromagnetic material that a typical MRI system cannot detect or disregards their presence on a medical device, such as a catheter. If a MRI system cannot detect or disregards the low-level paramagnetic or ferromagnetic material on a medical device, such as a catheter, the device will not be capable of being visualized as the anatomy is scanned during MRI.

Figure 4D:
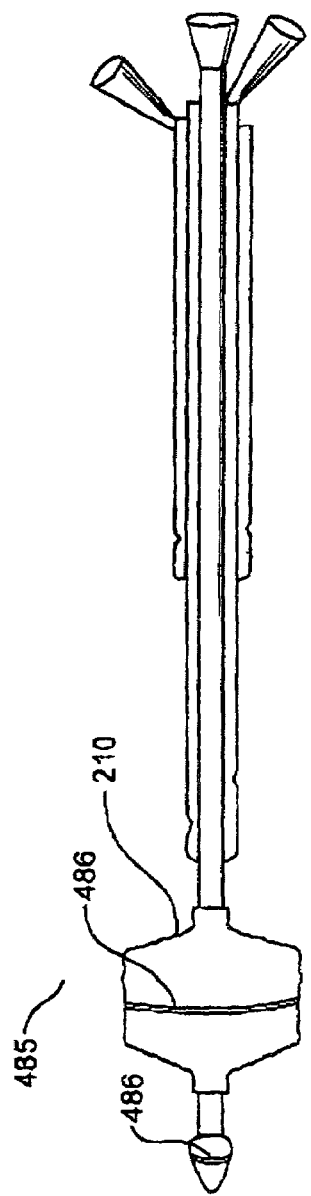
FIG. 4D illustrates an embodiment of a balloon catheter having a band of target markers embedded or attached thereto with the balloon of the catheter inflated.

FIG. 4D illustrates an embodiment having target markers 486 embedded or attached to a balloon catheter device 485. In this illustration, balloon 210 is fully deployed. Therefore, target markers 486 are spread about the inflated balloon's circumference. In this embodiment, target markers 486 include a very thin band of paramagnetic or ferromagnetic material that is embedded or attached to the perimeter of catheter 485 in two strategic locations. These two strategic locations may vary as long as orientation of catheter 485 can be determined based on the location of target markers 486. Target markers 486 are of such a low level of paramagnetic or ferromagnetic material that a typical MRI system cannot detect their presence (or disregards the signals) on a medical device, such as a catheter. If a MRI system cannot detect the low-level paramagnetic or ferromagnetic material on a medical device, such as a catheter, the device will not be capable of being visualized as the anatomy is scanned during MRI.

Figure 4E:
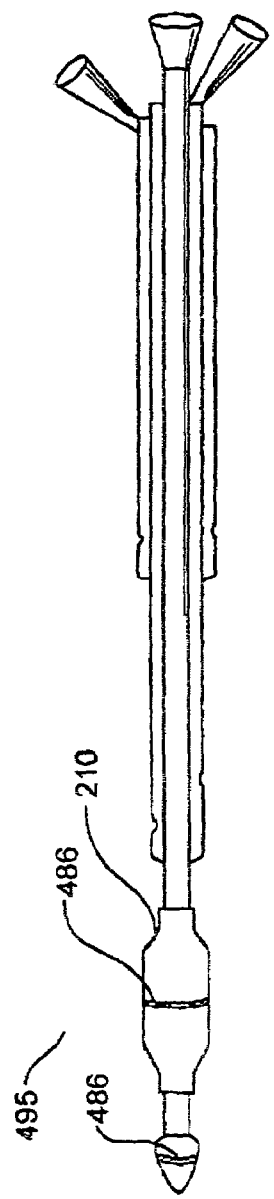
FIG. 4E illustrates an embodiment of a balloon catheter having a band of target markers embedded or attached thereto with the balloon of the catheter deflated.

FIG. 4E illustrates an embodiment having target markers 486 embedded or attached to a balloon catheter device 495. In this illustration, balloon 210 is deflated. Therefore, target markers 486 surround the deflated balloon's circumference. In this embodiment, target markers 486 include very thin bands of paramagnetic or ferromagnetic material that are embedded or attached to the perimeter of catheter 495 in a plurality of strategic locations, for example two. In this example, the two strategic locations may vary as long as orientation of catheter 495 can be determined based on the location of target markers 486. Target markers 486 are of such a low level of paramagnetic or ferromagnetic material that a typical MRI system cannot detect their presence (or is programmed to disregard the signals as noise) on a medical device, such as a catheter. If a MRI system cannot detect or disregards the low-level paramagnetic or ferromagnetic material on a medical device, such as a catheter, the device will not be capable of being visualized as the anatomy is scanned during MRI.

By having target markers 486 placed in strategic points on the balloon of catheter 485 or 495, when the balloon is being inflated, subsequent scans can determine the orientation and state of the balloon by the detection of the displaced target markers 486. This is due to the target markers 486 being further displaced as the balloon is inflated, i.e. the circumference is expanding upon inflation of the balloon. Once the location of target markers 486 and the orientation of the medical device is determined, a previously scanned image or information describing a detailed image of the medical device outside the anatomy can be either superimposed or the pixels of the anatomy replaced with those of the medical device. Therefore, a clear image of the medical device can be displayed with the correct position and orientation of the medical device as it is situated within the anatomy.

In one embodiment, it is necessary to only detect a portion of the plurality of strategically placed target markers in order to determine position and orientation of a medical device as situated within an anatomy. Since the location and orientation of the plurality of the strategically placed target markers are known in advance (as compared to the medical device and between each of the target markers), if only a portion of the strategically placed target markers are detected, based on the orientation and location relationships between the target markers and the medical device, the location and orientation of the medical device as situated in an anatomy can be determined.

In one embodiment that uses pre-scanner 360, images of the balloon catheter need to be taken when the balloon is both deflated and fully inflated. In one embodiment where geometric and image data is pre-loaded, many sets of data are stored for various inflation states for each stored device. Once the orientation is determined via target markers 486, a comparison of the stored inflation states is made for a particular device.

Referring to the system described in FIG. 3, a technique for imaging a medical device having otherwise non-detectable or typically disregadable markers for an MRI system is described with reference to FIGS. 4A-4E and the accompanying text, the catheter bodies having target markers such as described, to be inserted into an anatomy is scanned by pre-scanner 360. Pre-scanner 360 scans device 350 outside of an anatomy. Pre-scanner 360, after scanning device 350, transmits data to low-level detection processor 320. The data transmitted to low-level detection processor 320 includes geometrical information about device 350, such as length, width, height, etc. Along with the geometrical information transmitted to low-level detection processor 320, coordinates of target markers (in relation to the geometric information of the medical device) are also transmitted to processor 320.

In one embodiment, the target markers may include a continuous ring at strategic locations on the medical device. For a medical device such as balloon catheter 485 or 495 (illustrated in FIGS. 4D and 4E), the low-level ferromagnetic or paramagnetic material used for target markers may be placed at the following locations:

distal 0.1 mm ring on catheter tip;
0.1 mm ring on balloon proximal shoulder circumference;
0.1 mm ring on balloon distal shoulder circumference; and
0.1 mm ring-on $\frac{2}{3}^{rd}$ distal-taper circumference.

Figure 6:
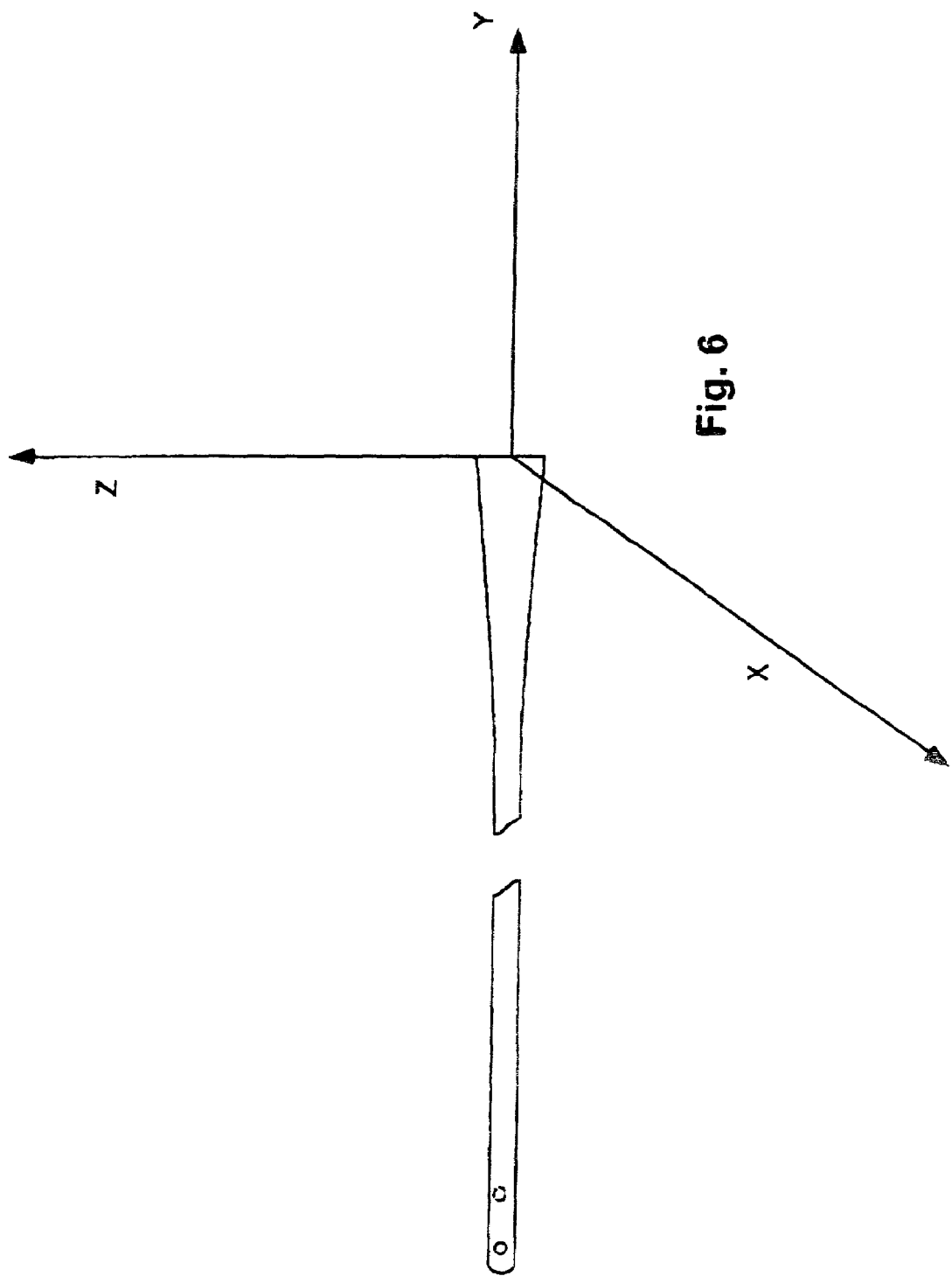
FIG. 6 illustrates an embodiment of a proximal end of a catheter having coordinates set at X=0, Y=0, Z=0.
Figure 7:
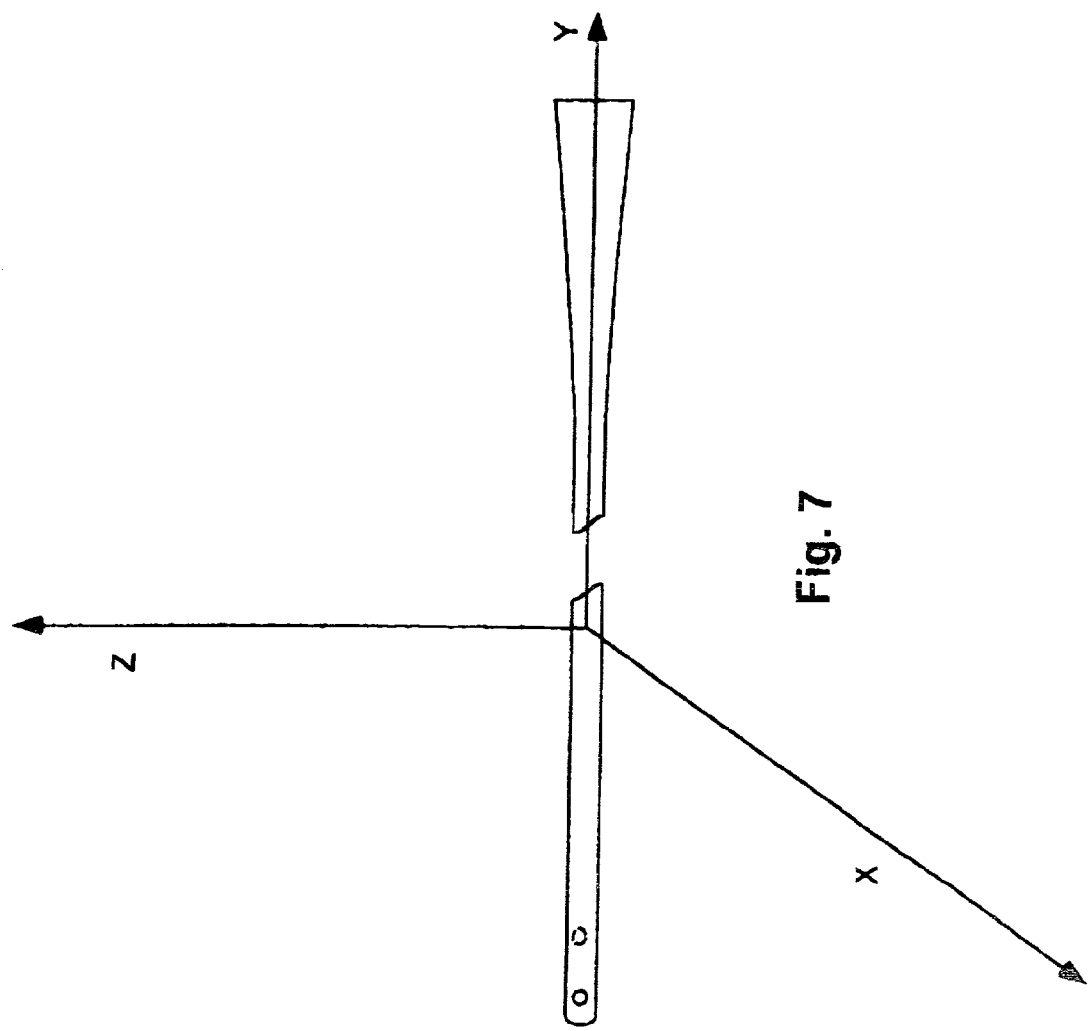
FIG. 7 illustrates an embodiment of the invention having a center of a medical device set as X=0, Y=0, Z=0.

In one embodiment, a three coordinate system, such as an X,Y, Z, coordinate system, is used to establish position. FIGS. 5-7 illustrate different initial settings for a three dimensional coordinate system. FIG. 5 illustrates an embodiment where a medical device's distal end has its coordinates set to X=0, Y=0, Z=0. FIG. 6 illustrates an embodiment having a proximal end of a medical device set at X=0, Y=0, Z=0. FIG. 7 illustrates an embodiment having a center of a medical device set as X=0, Y=0, Z=0. By determining the location of target markers on a medical device in a three-dimensional coordinate system, the orientation of the medical device can be determined.

Figure 8A:
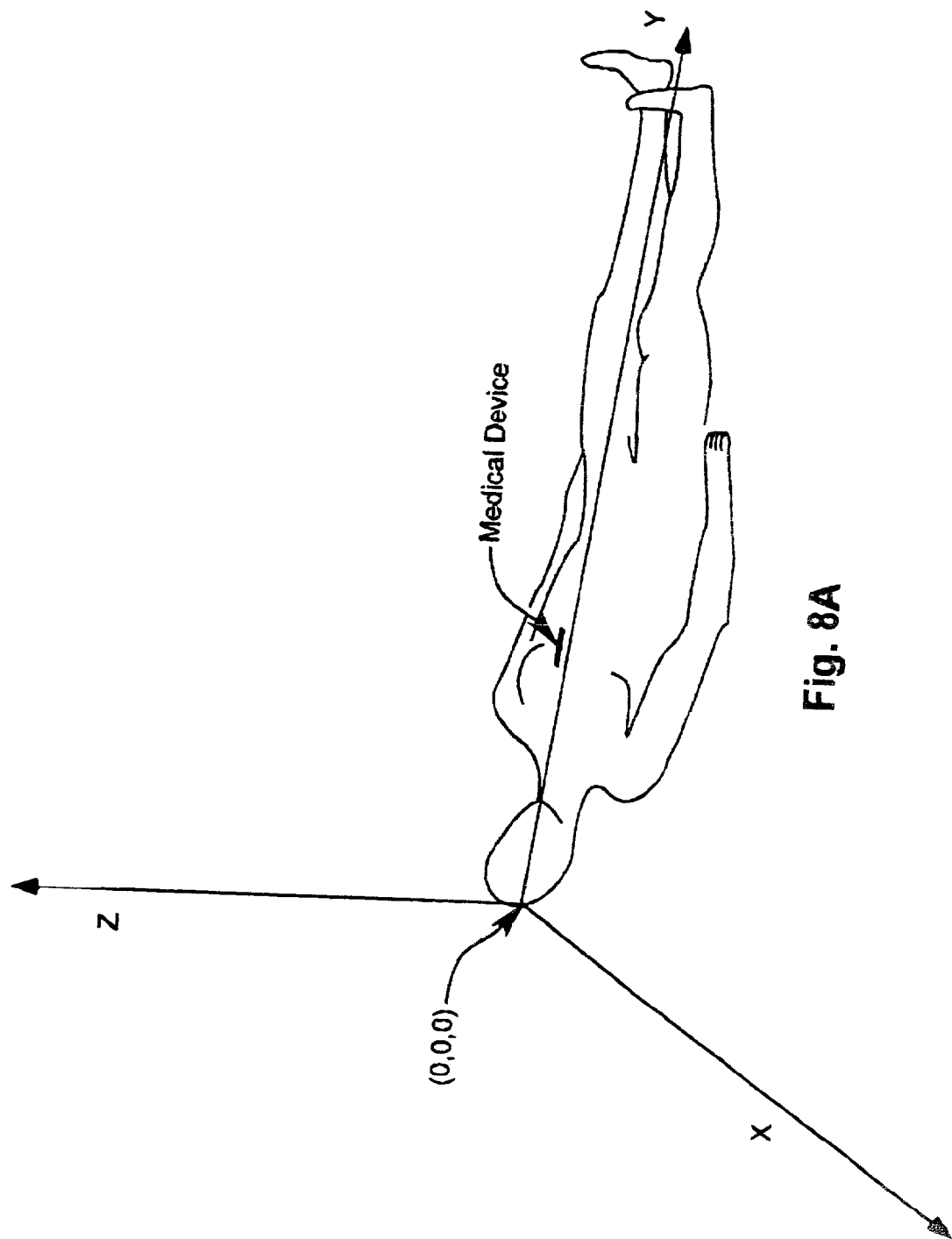
FIG. 8A illustrates an embodiment of the invention having an anatomy's head set as X=0, Y=0, Z=0.
Figure 8B:
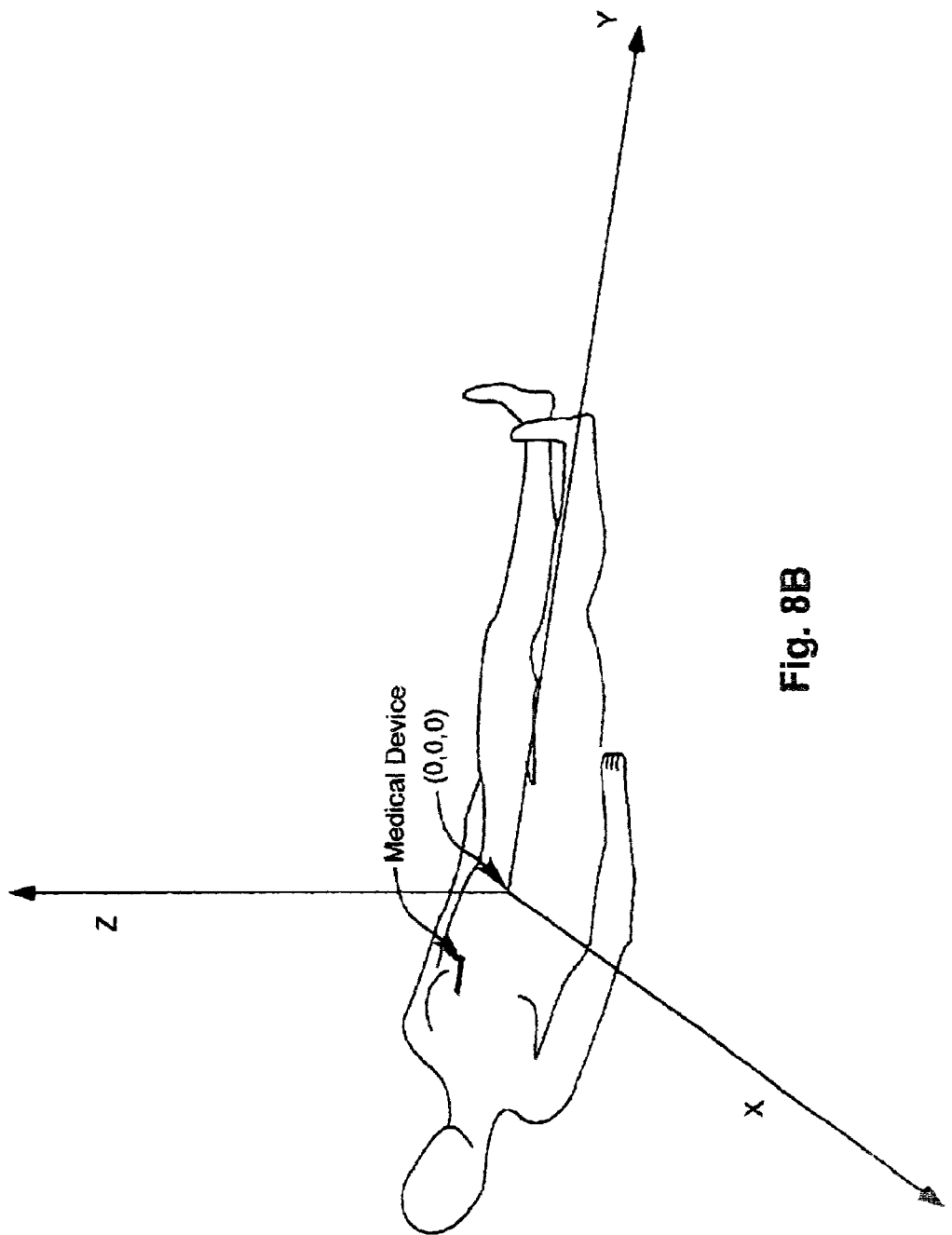
FIG. 8B illustrates an embodiment of the invention having an anatomy's center set as X=0, Y=0, Z=0.

FIG. 8A illustrates an embodiment having an anatomy's head set as X=0, Y=0, Z=0. FIG. 8B illustrates an embodiment having an anatomy's center set as X=0, Y=0, Z=0. In these embodiments, once the anatomy is scanned without a medical device, another scan is taken with the inserted medical device. The coordinates of the device in the anatomy is determined based on the target markers (the target markers coordinates are known). Therefore, the precise location and orientation of the inserted medical device can be determined relative to an anatomy in a three-dimensional coordinate system.

With the geometric information and the coordinates of target markers, low-level detection process 320 is capable of determining geometric orientation of device 350 within an anatomy based on the orientation of detected target markers 410 within an anatomy, in relation to the known geometric and target marker information.

In one embodiment, pre-scanner 360 scans device 350 outside an anatomy and stores a multi-dimensional (e.g., 2-D or 3-D) image of device 350 in memory-image processor 310. Upon scanner 330 scanning device in anatomy 340, and detecting the low-level target markers 410 from low-level detection process 320, image processor 310 can process the anatomy and device in anatomy 340 simultaneously. Process 320 can then determine the geometrical orientation of device 340 in the anatomy. Image processor 310 then creates a visual image of anatomy without the inserted device 340.

Process 320, however, already detected and determined the orientation of the device in anatomy. Therefore, in one embodiment, process 320 superimposes the stored multi-dimensional image of previously scanned device 350 on to the exact determined anatomy that the image processor detected the device in anatomy 340's location. In this embodiment, an accurate and informative visualization of the device in anatomy can then be displayed on display 380. Therefore, process 320, unlike typical MRI systems that disregard low-level signals as noise, uses the detected low-level signals to position (superimpose) a scanned image of device 350 according to its orientation in anatomy. By using a scanned image of device 350, this embodiment of the invention can clearly display device 350 accurately and precisely as it is positioned in the anatomy. One should note that the superimposed image may be updated as frequently as new information and orientation is determined. In one embodiment, process 320, instead of superimposing the stored multi-dimensional image data of device 350, can replace the pixels of the anatomy detected by scanner 330, with the pixels of the previously scanned three-dimension image data of device 350. In this embodiment, since the exact position of the device in the anatomy is determined, and the anatomy with the device not present is also determined, the pixels of the anatomy where the device is determined to be located can be removed and replaced with the scanned-in image of the device. Therefore, process 320, unlike typical MRI systems that disregard low-level signals as noise, uses the detected low-level signals to position (replace pixels) pixels of a scanned image of device 350 according to its orientation in anatomy. This results in a clear visualization that can be displayed on display 380. One should note that the pixels of the medical device and the anatomy can be updated as frequently as new information and orientation is determined. In one embodiment, various sets of information are stored for a balloon catheter in different states (i.e., deflated and inflated). Based on a comparison of a scanned balloon catheter, the closest stored data set is chosen for either superimposing or pixel replacement, depending on the embodiment. In one embodiment, known techniques such as interpolation and curve fitting can be used for the comparison between a scanned image in anatomy and stored image/geometrical data.

In one embodiment, a plurality of known medical devices geometrical and/or image data is pre-stored in memory in image processor 310. Therefore, a pre-scanned image or geometrical information of device 350 need not be transmitted to image processor 310. A user may select the device from a list, such as a drop-down menu, etc. of known devices via user control 370. Therefore, less processing time is necessary to superimpose a device image or replace pixels of anatomy with that of the medical device used in anatomy as compared to having to scan in the medical device and transfer the data. In another embodiment, a choice of resolutions for the medical device is given to a user from a list, such as a drop-down menu, etc. In this embodiment, pre-scanner 360 need not be coupled to system 300.

In one embodiment, target markers may be adhered or embedded into a medical device by means such as laser drilling and adhesion, or inserting a small number of target markers during typical manufacturing techniques for polymer medical devices.

In one embodiment, the target markers are made from paramagnetic materials such as dysprosium, gadolinium, and alloys and salts of these materials. Alternatively, ferromagnetic materials may be used for target markers such as iron, nickel, cobalt, and alloys of these materials. One should note that other paramagnetic or ferromagnetic materials can be used without diverging from embodiments of the invention.

In one embodiment, process 320 may be loaded into memory on a typical MRI system. Therefore, only small modifications are necessary to allow typical MRI systems to detect and display the low-level target markers (previously undetected or detected but disregarded as noise), and medical device images over, or instead of, portions of anatomy. Thus, if process 320 is loaded on a typical MRI system, the typical MRI system will be modified so that it can detect the low-level ferromagnetic or paramagnetic material and, therefore, not discard the low-level information as it normally would. Therefore, the cost of replacing MRI processing portions of a MRI system can be kept to a minimum.

Figure 9:
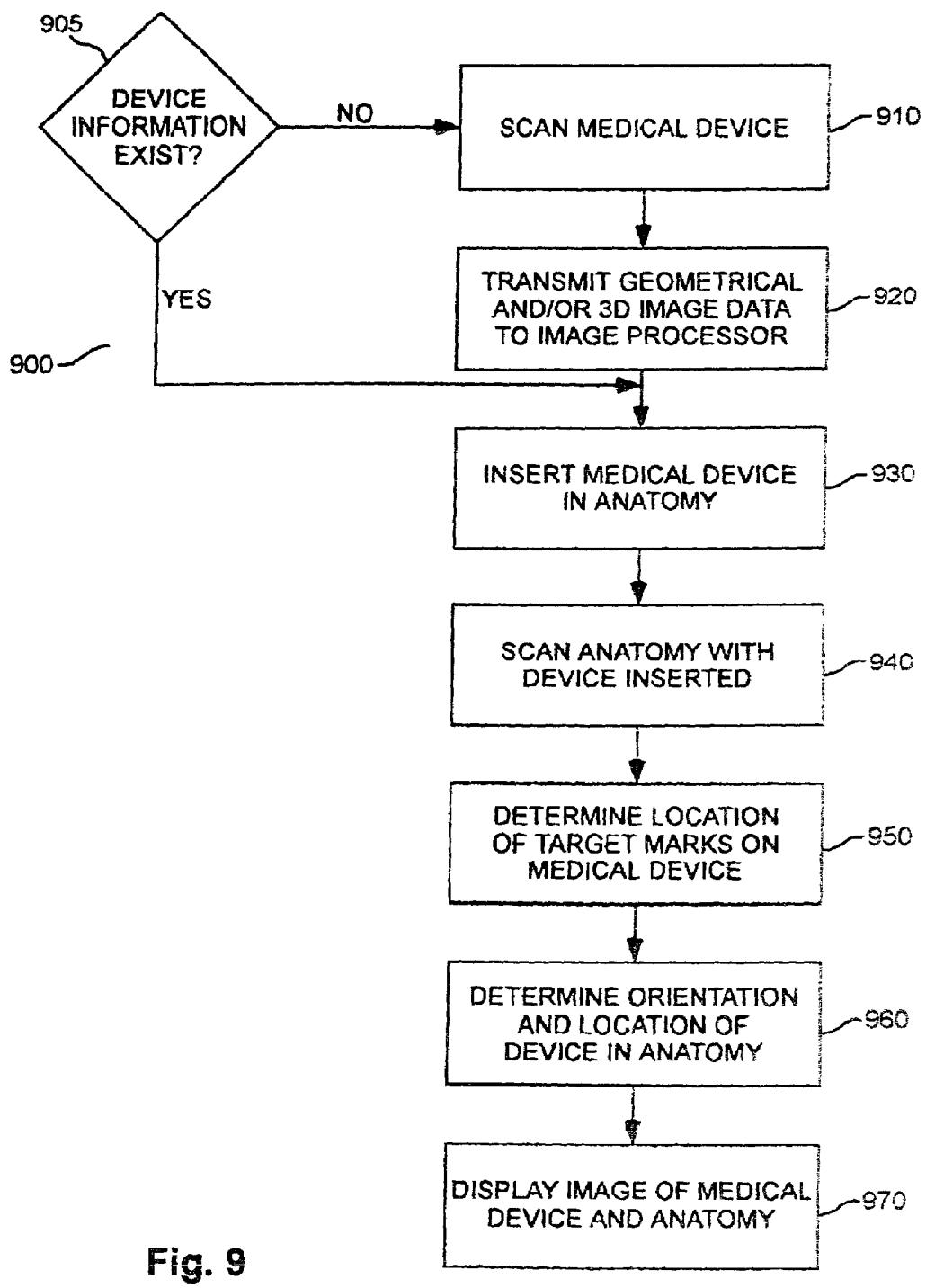
FIG. 9 illustrates a block diagram of an embodiment of the invention.

FIG. 9 illustrates a block diagram of an embodiment having process 900. Process 900 begins with block 905 that determines whether medical device geometric and/or image data already exists within the modified MRI system. If block 905 determines that the geometric and/or image data of the medical device does not exist, then process 900 continues with block 910. If the MRI system has a pre-scanning device, block 910 scans medical device for geometric and three-dimensional image data. If the MRI system does not have a pre-scanning device, process 900 would prompt a user to enter a data file for the information (the data file could either be already stored in memory, loaded from a CD-ROM, or loaded from any other means for loading the information, such as a tape drive, floppy drive, etc.) Process 900 would then continue with block 920. In block 920, the geometrical and three-dimension image data is transmitted to the modified image processor. Process 900 would then continue with block 930.

If block 905 determined that the geometrical and three-dimensional image data for the medical device already exists in the modified image processor, then process 900 continues with block 930. In block 930, the medical device would be inserted into the anatomy of the patient. After the medical device is inserted into the anatomy, process 900 continues with block 940. In block 940, the anatomy with the device inserted is scanned by the MRI system. After block 940 scans the anatomy, block 950 determines the location of the target markers located on the medical device within the anatomy. Based on the determined location of the target markers on the medical device in the anatomy, block 960 then determines the orientation and specific location of the device in the anatomy. It should be noted that either a single scan with the device in the anatomy or two separate scans (one of the anatomy without the device inserted, and one with the device inserted) can be implemented, depending on the user's preference. If a single scan is made, block 960 would determine the orientation of the device in the anatomy based on the anatomy and the location of the target markers within the anatomy. If two separate scans are made, a comparison of the two scans would be necessary for alignment purposes. Block 970 then displays the image of the medical device and the anatomy together on display.

In one embodiment, the displayed image of the medical device is super-imposed over the anatomy. This is accomplished by determining the exact location of the device within the anatomy, retrieving the geometric and/or image data of the medical device, and overlaying an image of the device in its relative location and orientation to the anatomy.

In another embodiment, the displayed image of the medical device is inserted in place of the pixels of the anatomy where the actual medical device is located. This is accomplished by determining the exact location of the device within the anatomy, retrieving the geometric and/or image data of the medical device, determining the pixels of the anatomy where the device is located, replacing the anatomical pixels with pixels of an image of the device in its relative location and orientation to the anatomy.

In one embodiment, an automatic medical device withdrawing tool (not shown) is coupled to a medical device already inserted in an anatomy. The automatic medical device withdrawing tool can be set manually or dynamically by an MRI system. The automatic medical device withdrawing tool automatically withdraws a medical device that was previously inserted into an anatomy at a constant pace. In one embodiment, the MRI system sets the pace of automatic withdrawal based on known information about the type of medical device that was inserted into an anatomy. The automatic medical device withdrawal tool can store a plurality of information based on parameters, such as device type, manufacturer, age of patient, etc. The plurality of information stored can be information such as length of device, stopping point for withdrawal, diameter of device, etc. The automatic medical device withdrawal tool automatically stops at a previous determined length of the medical device. In this way, the automatic medical device withdrawal tool is not withdrawn totally out of the patient. In one embodiment of the invention, the automatic medical device tool determined whether any resistance from a lumen that the medical device was inserted exists. If there is any abnormal resistance, the tool alerts a user and ceases to withdraw the medical device.

The above embodiments can also be stored on a device or machine-readable medium and be read by a machine to perform instructions. The machine-readable medium includes any mechanism that provides (i.e., stores and/or transmits) information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.). The device or machine-readable medium may include a solid state memory device and/or a rotating magnetic or optical disk. The device or machine-readable medium may be distributed when partitions of instructions have been separated into different machines, such as across an interconnection of computers.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A system comprising:
   a magnetic resonance imaging (MRI) processor, the processor including an MRI low-level signal detection process stored in a memory;
   a MRI scanner coupled to the processor;
   a control unit coupled to the processor;
   a display coupled to the processor; and
   a medical device adapted to insert into an anatomy, the medical device having a plurality of target markers, wherein geometric information for the plurality of target markers is stored in the memory prior to insertion of the medical device into the anatomy, and wherein MRI signals of the plurality of target markers within the anatomy are not detectable or are disregardable as noise for the system (a) without the MRI low-level signal detection process and (b) without using the stored geometric information of the plurality of target markers prior to insertion of the medical device into the anatomy to lower an MRI signal detection threshold.

2. The system of claim 1, further comprising a pre-scanning device coupled to the processor.

3. The system of claim 2, wherein the pre-scanning device is to transmit at least one of a plurality of geometric data, a plurality of image data, a plurality of geometric data and a plurality of image data of the medical device and the plurality of target markers to the processor.

4. The system of claim 1, wherein the plurality of target markers comprise at least one of ferromagnetic and paramagnetic material.

5. The system of claim 4, wherein MRI signals of the plurality of target markers are disregarded by the system operating between 0.2 and 5.0 Tesla.

6. The system of claim 1, wherein the medical device is one of a fluid delivering catheter, a stent delivering device, a photographic device and a balloon catheter.

7. The system of claim 6, wherein the medical device comprises a polymer material.

8. The system of claim 7, wherein the medical device is expandable.

9. The system of claim 1, wherein an orientation and a location of the medical device in relation to the anatomy is determinable based on a location of the plurality of target markers.

10. The system of claim 1, wherein an image of the medical device is superimposed on an image of the anatomy, the superimposed image having the same orientation and location that the medical device has within the anatomy.

11. The system of claim 1, wherein a plurality of pixels of the medical device replace a plurality of pixels of an image of the anatomy at a same location that the medical device is located within the anatomy, the plurality of pixels of the medical device having the same orientation that the medical device has within the anatomy.

12. The system of claim 1, wherein the memory stores one of a plurality of geometric data, a plurality of image data, and a plurality of geometric data and a plurality of image data of the medical device.

13. The system of claim 1, wherein the MRI low-level signal detection process adjusts the signal detection threshold to detect a low-level MRI signal produced from the target markers.

14. The system of claim 13, wherein a non-adjusted signal threshold will one of disregard or fail to detect the low-level MRI signal produced from the target markers.

15. The system of claim 1, wherein the MRI low-level signal detection process determines to recognize low-level MRI signals returned from the target markers upon a match from a comparison of known geometric data from the target markers with returned low-level MRI signals.

16. A method comprising:
   inserting a medical device into an anatomy, the medical device having a plurality of target markers;
   storing information for the medical device and the plurality of target markers in a memory prior to insertion of the medical device into the anatomy;
   scanning a magnetic resonance image (MRI) of the anatomy;
   processing the scanned image by a MRI processor coupled to the memory;
   determining a location and orientation of the medical device inserted in the anatomy in relation to the anatomy based on the plurality of target markers; and
   displaying an image of the medical device within the anatomy, including superimposing the medical device on the anatomy using the information for the medical device stored in the memory prior to insertion of the medical device into the anatomy.

17. The method of claim 16, further comprising:
   pre-scanning the medical device before inserting the medical device into the anatomy; and
   transmitting one of a plurality of geometric data, a plurality of image data, or a plurality of geometric data and a plurality of image data of the medical device and the plurality of target markers to the MRI processor.

18. The method of claim 16, wherein the plurality of target markers comprise at least one of ferromagnetic and paramagnetic material.

19. The method of claim 18, wherein MRI signals of the plurality of target markers are one of not detectable and disregarded by an MRI system operating between 0.2 and 5.0 Tesla.

20. The method of claim 16, wherein the medical device is one of a fluid delivering catheter, a stent delivering device, a photographic device and a balloon catheter.

21. The method of claim 20, wherein the medical device comprises a polymer material.

22. The method of claim 20, wherein the medical device is expandable.

23. The method of claim 16, further including superimposing a stored image of the medical device over an image of the anatomy, the superimposed image having the same orientation and location that the medical device has within the anatomy.

24. The method of claim 16, further including replacing a plurality of pixels of an image of the anatomy with a plurality of pixels of the medical device at the same location that the medical device is located within the anatomy, the plurality of pixels of the medical device having the same orientation that the medical device has within the anatomy.

25. The method of claim 16, wherein, prior to insertion of the medical device into the anatomy, the memory stores one of a plurality of geometric data, a plurality of image data, and a plurality of geometric data and a plurality of image data of the medical device and the plurality of target markers.

26. The method of claim 16, wherein processing the scanned image further includes:
adjusting a signal detection threshold to detect low-level MRI signals produced from the plurality of target markers, wherein if the signal detection threshold is unadjusted the low-level MRI signals produced from the plurality of target markers will be disregarded.

27. An apparatus comprising a machine-readable medium storing instructions which, when executed by a magnetic resonance imaging (MRI) system, cause the MRI system to perform operations comprising:
storing geometric information for a plurality of target markers of a medical device in a memory prior to insertion of the medical device into an anatomy;
scanning a magnetic resonance image of the anatomy with the medical device inserted into the anatomy;
processing the scanned image by a MRI processor coupled to the memory, the MRI processor having an MRI low-level signal detection process;
determining a location and orientation of the medical device in relation to the anatomy based on the geometric information of the plurality of target markers; and
displaying an image of the medical device within the anatomy, wherein MRI signals of the plurality of target markers within the anatomy are undetectable or disregardable as noise for the MRI system without using the stored geometric information of the plurality of target markers prior to insertion of the medical device into the anatomy to lower an MRI signal detection threshold.

28. The apparatus of claim 27, further containing instructions which, when executed by the MRI system, cause the MRI system to perform operations including:
pre-scanning the medical device before the medical device is inserted in the anatomy;
transmitting one of a plurality of geometric data, a plurality of image data, and a plurality of geometric data and a plurality of image data of the medical device and the plurality of target markers to the MRI processor; and
withdrawing the medical device from the anatomy at a dynamically adjusted pace.

29. The apparatus of claim 27, wherein the plurality of target markers comprise at least one of ferromagnetic and paramagnetic material.

30. The apparatus of claim 29, wherein the MRI signals of the plurality of target markers are one of not detectable and disregarded by the MRI system operating between 0.2 and 5.0 Tesla.

31. The apparatus of claim 27, wherein the medical device is one of a fluid delivering catheter, a stent delivering device, a photographic device and a balloon catheter.

32. The apparatus of claim 31, wherein the medical device comprises a polymer material.

33. The apparatus of claim 31, wherein the medical device is expandable.

34. The apparatus of claim 27, further containing instructions which, when executed by the MRI system, cause the MRI system to perform operations including:
superimposing an image of the medical device over an image of the anatomy, the superimposed image has the same location and orientation that the medical device has within the anatomy.

35. The apparatus of claim 27, further containing instructions which, when executed by the MRI system, cause the machine MRI system to perform operations including:
replacing a plurality of pixels of an image of the anatomy with a plurality of pixels of the medical device, the plurality of pixels of the medical device having the same location and orientation that the medical device has within the anatomy.

36. The apparatus of claim 27, wherein the memory stores one of a plurality of geometric data, a plurality of image data, and a plurality of geometric data and a plurality of image data of the medical device.

37. The apparatus of claim 27, wherein the MRI low-level signal detection process adjusts the signal detection threshold to detect a low-level MRI signal produced from the target markers.

38. An apparatus comprising a machine-readable medium storing instructions which, when executed by a MRI system, cause the MRI system to perform operations comprising:
storing geometric information for a medical device and a plurality of target markers of a medical device in a memory prior to insertion of the medical device into an anatomy;
scanning a magnetic resonance image of the anatomy with the medical device inserted;
processing the scanned image by a MRI processor coupled to the memory, the MRI processor having an MRI low-level signal detection process;
determining a location and orientation of the medical device in relation to the anatomy based on detection of the plurality of target markers in relation to the medical device and each of the plurality of target markers; and
displaying an image of the medical device within the anatomy, wherein MRI signals of the plurality of target markers within the anatomy are undetectable or disregardable as noise for the MRI system without the MRI low-level signal detection process and without using the geometric information of the plurality of target markers to lower an MRI signal detection threshold.

39. The apparatus of claim 38, wherein the MRI low-level signal detection process adjusts the signal detection threshold to detect a low-level MRI signal produced from the plurality of target markers.

40. A system comprising:
- a magnetic resonance imaging (MRI) processor, the processor including an MRI low-level signal detection process stored in a memory;
- a MRI scanner coupled to the processor;
- a control unit coupled to the processor;
- a display coupled to the processor; and
- a medical device to insert into an anatomy, the medical device having a plurality of target markers, wherein geometric information for the plurality of target markers is stored in the memory prior to insertion of the medical device into the anatomy, and wherein MRI signals of the plurality of target markers within the anatomy are undetectable or disregardable as noise for an MRI system without the MRI low-level signal detection process and without using the stored geometric information of the plurality of target markers to lower an MRI signal detection threshold, and wherein the system is to use the geometric information of the plurality of target markers to determine location and orientation of the medical device in relation to the anatomy.

41. The system of claim 40, wherein the MRI low-level signal detection process adjusts the signal detection threshold to detect a low-level MRI signal produced from the target markers.

42. The system of claim 41, wherein geometric information of the medical device and a position of the detected plurality of target markers are used to display an image of the medical device superimposed on an image of the anatomy, the image representative of the actual location and orientation of the medical device in the anatomy.

* * * * *